United States Patent
Choi et al.

(10) Patent No.: US 10,172,943 B2
(45) Date of Patent: Jan. 8, 2019

(54) IRINOTECAN-LOADED DUAL-REVERSE THERMOSENSITIVE HYDROGEL COMPOSITION

(71) Applicant: Industry-University Cooperation Foundation Hanyang University ERICA Campus, Ansan (KR)

(72) Inventors: Han-Gon Choi, Seoul (KR); Fakhar Ud Din, Ansan (KR); Dong Wuk Kim, Ansan (KR); Dong Shik Kim, Suwon (KR); Chul Soon Yong, Daegu (KR); Jong Oh Kim, Daegu (KR); Yu-Kyoung Oh, Seoul (KR)

(73) Assignee: INDUSTRY—UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 0 days.

(21) Appl. No.: 15/517,013

(22) PCT Filed: Jan. 21, 2016

(86) PCT No.: PCT/KR2016/000668
§ 371 (c)(1),
(2) Date: Apr. 5, 2017

(87) PCT Pub. No.: WO2017/030254
PCT Pub. Date: Feb. 23, 2017

(65) Prior Publication Data
US 2018/0147282 A1 May 31, 2018

(30) Foreign Application Priority Data
Aug. 18, 2015 (KR) .................. 10-2015-0116321

(51) Int. Cl.
| | | |
|---|---|---|
| *A61K 31/4745* | (2006.01) | |
| *A61K 47/22* | (2006.01) | |
| *A61K 9/02* | (2006.01) | |
| *A61K 47/34* | (2017.01) | |
| *A61K 47/44* | (2017.01) | |
| *A61K 9/00* | (2006.01) | |
| *A61K 9/06* | (2006.01) | |
| *A61K 9/51* | (2006.01) | |
| *A61P 35/00* | (2006.01) | |

(52) U.S. Cl.
CPC ............ *A61K 47/22* (2013.01); *A61K 9/0019* (2013.01); *A61K 9/0031* (2013.01); *A61K 9/02* (2013.01); *A61K 9/06* (2013.01); *A61K 9/5123* (2013.01); *A61K 31/4745* (2013.01); *A61K 47/34* (2013.01); *A61K 47/44* (2013.01); *A61P 35/00* (2018.01)

(58) Field of Classification Search
CPC .......................... A61K 31/4745; C07D 491/22

USPC ............................................. 514/283; 546/48
See application file for complete search history.

(56) References Cited

U.S. PATENT DOCUMENTS

| | | | |
|---|---|---|---|
| 6,761,900 B2 | 7/2004 | Shudo | |
| 7,592,021 B2 | 9/2009 | Shankar | |
| 7,976,847 B2 | 7/2011 | Southard | |
| 2012/0244222 A1 | 9/2012 | Altreuter | |

FOREIGN PATENT DOCUMENTS

| | | |
|---|---|---|
| CN | 101342142 | 1/2009 |
| EP | 1752150 | 2/2007 |
| JP | 4885715 | 2/2012 |
| KR | 10-1999-0079175 | 11/1999 |
| KR | 10-2003-0071117 | 9/2003 |
| KR | 10-2013-0110476 | 10/2013 |
| KR | 10-2014-0022025 | 2/2014 |
| WO | 2011-129627 | 10/2011 |

OTHER PUBLICATIONS

Casado, A. et al.: Formulation and in vitro characterization of thermosensitive liposomes for the delivery of irinotecan. J. of Pharmaceutical Sci., vol. 103, pp. 3127-3138, 2014.*
U.S. Appl. No. 60/275,213, filed Mar. 12, 2001, Shudo.
Fakhar ud Din et al., "Development of a novel solid lipid nanoparticlesloaded dual-reverse thermosensitive nanomicelle for intramuscular administration with sustained release and reduced toxicity", RSC Advances, Apr. 2015, p. 43687-43694
Fakhar ud Din et al., "Novel dual-reverse thermosensitive solid lipid nanoparticle-loaded hydrogel for rectal administration of flurbiprofen with improved bioavailability and reduced initial burst effect", European Journal, May 2015, p. 64-72.
Norbert Marschner et al., "Oxaliplatin-based first-line chemotherapy is associated with improved overall survival compared to first-line treatment with irinotecan-based chemotherapy in patients with metastatic colorectal cancer—Results from a prospective cohort study", Clinical Epidemiology, Apr. 20, 2015, 7, pp. 295-303.
Lalitha Iyer et al., "Biliary transport of irinotecan and metabolites in normal and P-glycoprotein-deficient mice", Cancer Chemother Pharmacol, Apr. 2002, 49, pp. 336-341.
Jing-Ji Xuan et al., "Rheological characterization and in vivo evaluation of thermosensitive poloxamer-based hydrogel for intramuscular injection of piroxicam", International Journal of Pharmaceutics, 395, Available online Jun. 4, 2010, pp. 317-323.
Jun-Kyu Park et al., "Thermosensitive Chitosan-based Hydrogel with Growth Factor as Adhesion Barrier", Polymer (Korea), vol. 39, No. 3, pp. 480-486, May 2015.

(Continued)

*Primary Examiner* — Charanjit Aulakh
(74) *Attorney, Agent, or Firm* — Lex IP Meister, PLLC

(57) ABSTRACT

Provided is an irinotecan-loaded dual-reverse thermosensitive formulation, which is a dual-reverse thermosensitive hydrogel composition including nanoparticles including irinotecan and lipids; a hydrogel; and a stabilizer.

8 Claims, 6 Drawing Sheets

(1 of 6 Drawing Sheet(s) Filed in Color)

(56) References Cited

OTHER PUBLICATIONS

X. Zhang et al., "Biofunctionalized polymer-lipid supported mesoporous silica nanoparticles for release of chemotherapeutics in multidrug resistant cancer cells", Biomaterials, vol. 35, No. 11, pp. 3650-3665, Jan. 24, 2014, XP028609479, Elsevier.
EPO, Extended European search report of EP 16837198.7 dated Apr. 23, 2018.

* cited by examiner

[FIG. 1]
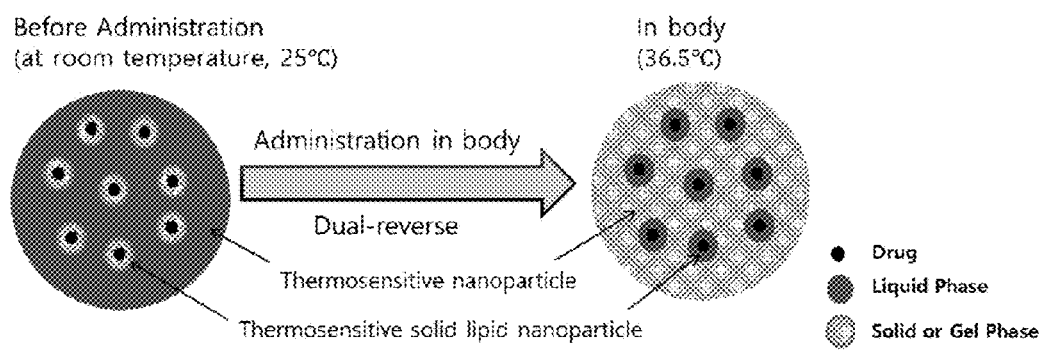

[FIG. 2]
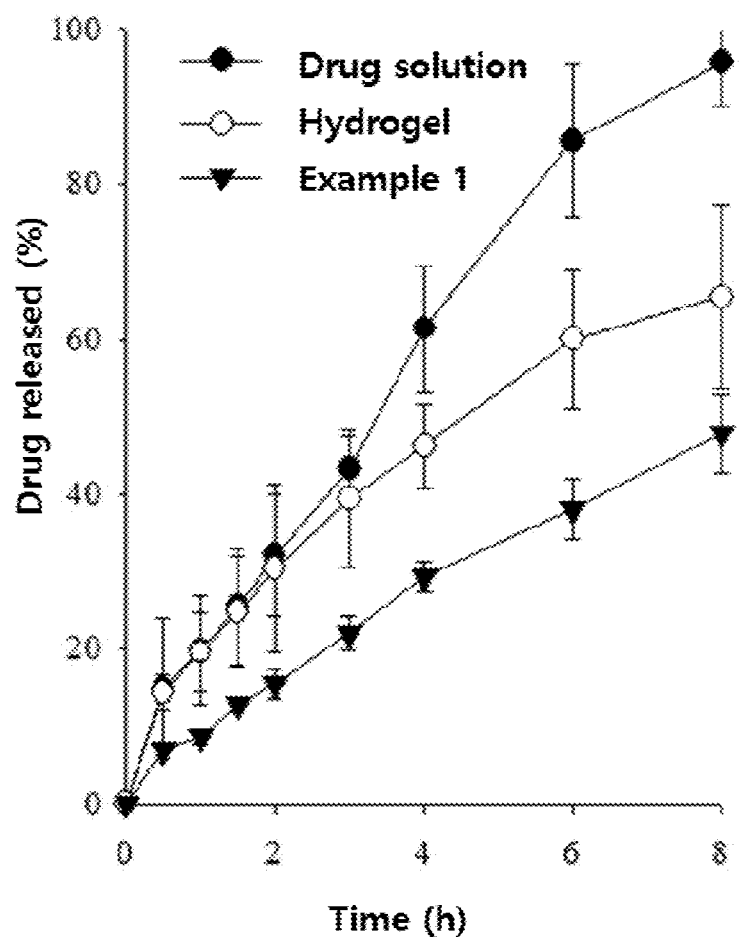

[FIG. 3]
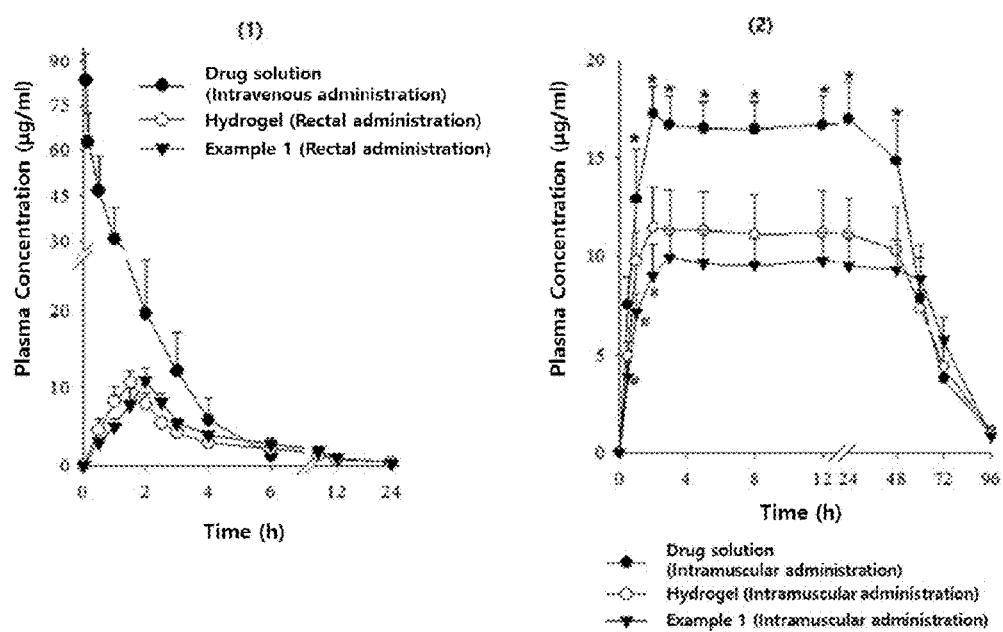
Each value represents the mean ± S.D. (n=6).
Significance at *p <0.05 as compared with Example and hydrogel.
Significance at *p <0.05 as compared with hydrogel.

[FIG. 4]
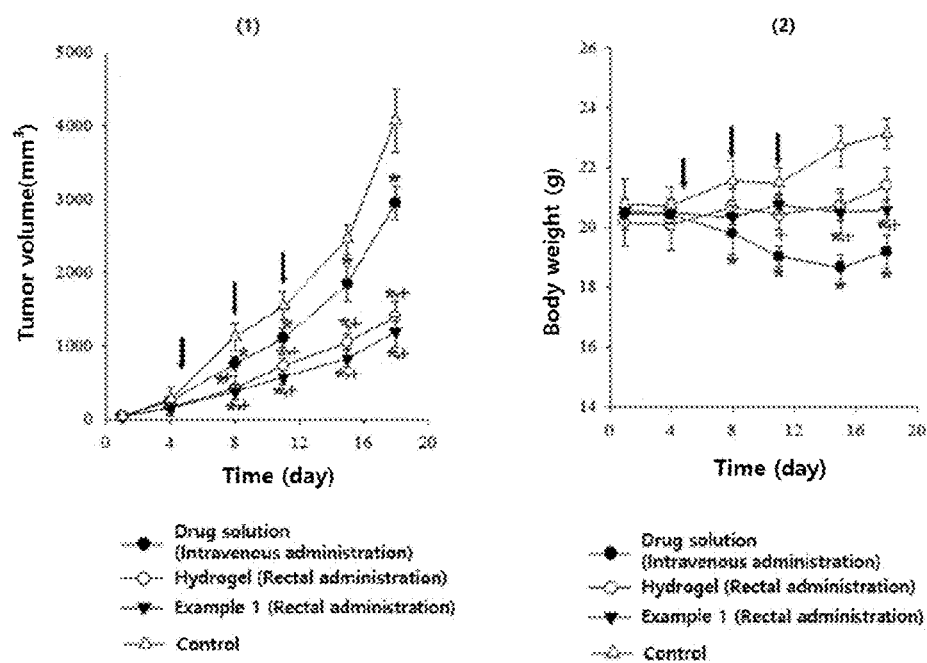
Each values expressed as mean ± standard deviation (n=6)
Significance at *p <0.05 as compared with control.
Significance at *p <0.05 as compared with drug solution.

[FIG. 5]
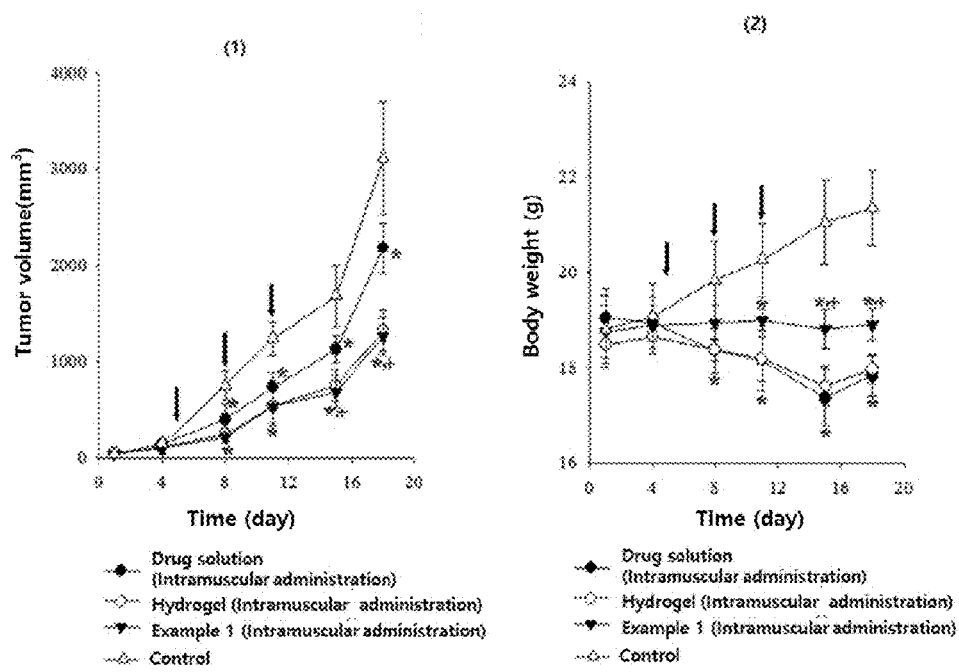
(1)
Each values expressed as mean ± standard deviation (n=6)
Significance at *p <0.05 as compared with control.
Significance at *p <0.05 as compared with drug solution.
(2)
Each values expressed as mean ± standard deviation (n=6)
Significance at *p <0.05 as compared with control.
Significance at *p <0.05 as compared with drug solution.

[FIG. 6]

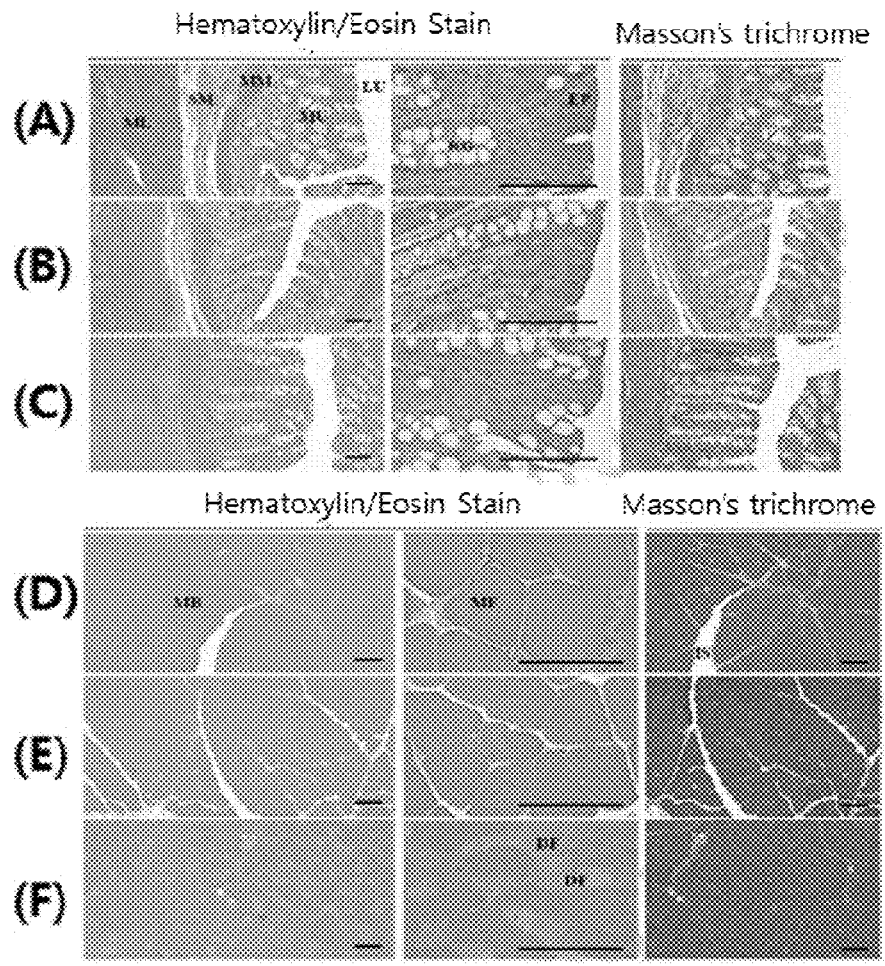

MB = muscle bundle; MF = muscle fibre; Scale bars = 120 μm.
(A), Rectal tissue not administered (control)
(B), Rectal tissue after rectal administration of Example 1
(C), Rectal tissue after rectal administration of hydrogel
(D), Muscle tissue not administered (control)
(E), Muscle tissue after intramuscular administration of Example 1
(F), Muscle tissue after intramuscular administration of hydrogel

IRINOTECAN-LOADED DUAL-REVERSE THERMOSENSITIVE HYDROGEL COMPOSITION

TECHNICAL FIELD

The present invention relates to a dual-reverse thermosensitive hydrogel composition including irinotecan as an active ingredient. More particularly, the present invention relates to a formulation for intramuscular or rectal administration, in which irinotecan-loaded thermosensitive solid lipid nanoparticles are dispersed in a thermosensitive hydrogel. That is, the thermosensitive hydrogel is prepared by mixing two or more poloxamers and a stabilizer Tween 80 to have a gelation temperature of 30° C. to 36° C., and then mixed with irinotecan as the active ingredient and a lipid mixture of tricaprin and triethanolamine, thereby preparing the thermosensitive solid lipid nanoparticle-dispersed formulation having a melting point of 30° C. to 36° C. The solid lipid nanoparticles and the hydrogel exist as a solid form and a liquid form at room temperature, respectively. On the contrary, the former is melted to a liquid form while the latter is altered to a gel in the body. Therefore, release of irinotecan is doubly regulated to resolve the initial burst effect. In addition, the toxic irinotecan avoids a direct contact with muscle tissues, leading to no damage to rectal and muscle tissues. Accordingly, the irinotecan-loaded dual-reverse thermosensitive hydrogel composition for intramuscular or rectal administration improves mucosal damage and increases efficacy upon rectal administration and retards release of the drug upon intramuscular administration to maintain the drug efficacy for a long time.

BACKGROUND ART

Irinotecan, a water-soluble camptothecin derivative, exhibits excellent anticancer activity through inhibition of topoisomerase-1 enzyme. At present, irinotecan is an anticancer agent frequently used for colon cancer or rectal cancer (Marschner et al., 2015) and marketed as an intravenous infusion (Iyer et al., 2002). However, this drug includes many anticancer side effects of other general anticancer agents. Further, there are attempts to increase drug efficacy by sustained release of a drug via intramuscular injection of the toxic drug such as irinotecan, etc. encapsulated in a hydrogel (Xuan et al., 2010). This hydrogel formulation is a formulation greatly increasing bioavailability while sustaining the drug release. However, there is a concern about side effects of the drug, which are caused by very high blood concentrations due to initial burst effect whereby the drug is initially released at a high concentration. Further, there is a problem that when used for a long time, muscle tissues may be greatly damaged because of direct contact of the toxic drug with muscle tissues.

Accordingly, there is a need for a new formulation capable of sustaining the efficacy of the toxic irinotecan and improving initial burst effect of the drug and safety to body tissues at the same time.

DISCLOSURE

Technical Problem

An object of the present invention is to provide a dual-reverse thermosensitive hydrogel composition having a gelation temperature of 30 to 36° C., the composition including nanoparticles including irinotecan as an active ingredient and tricaprin, triethanolamine, or a lipid mixture thereof having a melting point of 30° C. to 36° C.; poloxamer 188, poloxamer 407, or a mixture thereof; and a stabilizer, and a formulation of the dual-reverse thermosensitive hydrogel composition, thereby controlling initial burst of the drug and improving safety to body tissues.

Technical Solution

The present invention provides an irinotecan-loaded dual-reverse thermosensitive hydrogel composition having a gelation temperature of 30 to 36° C., including nanoparticles including irinotecan as an active ingredient and a lipid having a melting point of 30 to 36° C., which is selected from the group consisting of tricaprin, triethanolamine, and a mixture thereof; poloxamer 188, poloxamer 407, or a mixture thereof; and Tween 80. Preferably, the irinotecan-loaded dual-reverse thermosensitive hydrogel composition may include 0.1% by weight to 5% by weight of the irinotecan; 5% by weight to 9.9% by weight of the tricaprin, the triethanolamine, or the lipid mixture thereof; 30% by weight to 34% by weight of the poloxamer 188, the poloxamer 407, or the mixture thereof; and 2% by weight to 6% by weight of Tween 80, based on the total weight of the composition. Preferably, the lipid mixture may be a lipid obtained by mixing the tricaprin and the triethanolamine at a ratio of 99.9:0.1 to 10:90. Preferably, the irinotecan-loaded dual-reverse thermosensitive hydrogel composition may include both of the poloxamer 188 and the poloxamer 407. More preferably, the dual-reverse thermosensitive hydrogel composition may be administered to the muscle or rectum.

Further, the present invention provides an irinotecan-loaded dual-reverse thermosensitive formulation having a gelation temperature of 30 to 36° C., including nanoparticles including irinotecan as an active ingredient and tricaprin, triethanolamine, or a mixture thereof having a melting point of 30 to 36° C.; poloxamer 188, poloxamer 407, or a mixture thereof; and a stabilizer.

Preferably, the stabilizer is Tween 80.

Preferably, the formulation is an irinotecan-loaded dual-reverse thermosensitive formulation having a gelation temperature of 30 to 36° C., including nanoparticles including 0.1% by weight to 5% by weight of the irinotecan as an active ingredient and 5% by weight to 9.9% by weight of the tricaprin, the triethanolamine, or the mixture thereof having a melting point of 30 to 36° C.; 30% by weight to 36% by weight of the poloxamer 188, the poloxamer 407, or the mixture thereof; and 2% by weight to 6% by weight of Tween 80.

More preferably, the lipid mixture may be a lipid obtained by mixing the tricaprin and the triethanolamine at a ratio of 99.9:0.1 to 10:90.

More preferably, the irinotecan-loaded dual-reverse thermosensitive formulation is characterized by including both of the poloxamer 188 and the poloxamer 407.

Preferably, the formulation is characterized by being administered to the muscle or rectum.

The nanoparticles according to the present invention include the drug and the lipid, and a size of the nanoparticles may vary depending on a surfactant. The size may be preferably 130 nm to 170 nm, and more preferably 135 nm to 140 nm.

The dual-reverse thermosensitive formulation according to the present invention may include irinotecan as an active ingredient.

According to still another embodiment of the present invention, the formulation may include 0.1% by weight to 5% by weight of irinotecan, based on the total weight of the formulation. When the content of the active ingredient is less than 0.1% by weight, a very high dose of the formulation must be administered in order to obtain effective efficacy of the drug. In consideration of physical stability, such as a precipitation problem of the nanoparticles of the dual-reverse thermosensitive formulation, the content of the drug is appropriately selected from the above range. For example, when the content of the drug is more than 5% by weight, the content of the lipid nanoparticles is increased to 10% or more, thereby generating a problem in physical stability, such as precipitation of the lipid nanoparticles.

The dual-reverse thermosensitive formulation according to the present invention may include a lipid, and preferably, tricaprin, triethanolamine, or a mixture thereof.

Further, a content of the lipid must be 2 times or more than that of the drug, and in consideration of the content of irinotecan, the lipid may be included in an amount of 5% by weight to 9.9% by weight, based on the total weight of the dual-reverse thermosensitive formulation of the present invention. When the content of the lipid mixture is less than twice the content of the drug, drug encapsulation efficiency may be greatly decreased.

According to an embodiment of the present invention, the dual-reverse thermosensitive formulation may include 5% by weight to 9.9% by weight of the lipid, based on the total weight of the formulation. According to another embodiment of the present invention, the lipid may be one or more selected from the group consisting of tricaprin and triethanolamine. Preferably, the formulation may include a mixture of the tricaprin and the triethanolamine at a weight ratio of 99.9:0.1 to 10:90.

The dual-reverse thermosensitive formulation according to the present invention may include a polymer hydrogel. Preferably, the polymer hydrogel may be a poloxamer, and more preferably, the polymer hydrogel may be one or more selected from the group consisting of poloxamer 188 and poloxamer 407.

According to still another embodiment of the present invention, the dual-reverse thermosensitive formulation may include 30% by weight to 34% by weight of the polymer hydrogel, based on the total weight of the formulation.

As a base in the dual-reverse thermosensitive hydrogel formulation according to the present invention, one or more of non-toxic poloxamer 188 and poloxamer 407 may be used. The dual-reverse thermosensitive formulation of the present invention may include the base in an amount of 30% by weight to 34% by weight to have a gelation temperature of 30 to 36° C. When the content of the poloxamer mixed base is more than 34% by weight, the gelation temperature becomes lower than 30° C., and therefore, the dual-reverse thermosensitive formulation is in a gel state at room temperature and administration is very difficult. When the content of the poloxamer mixed base is less than 30% by weight, the gelation temperature becomes higher than 36° C., the formulation exists as a liquid form even in the body, and thus dissolution of the drug is not effectively controlled. Accordingly, it is difficult to control initial burst effect and to avoid direct contact of the drug with the body tissues.

The dual-reverse thermosensitive formulation according to the present invention is characterized in that the nanoparticles including the irinotecan drug and the lipid are included in the polymer hydrogel and a gelation temperature is 30 to 36° C. The nanoparticles may exist in the polymer hydrogel by mixing, dispersing, or blending, but is not limited thereto.

Preferably, the lipid included in the nanoparticles may have a melting point of 30° C. to 36° C. When the melting point of the lipid mixture is lower than 30° C., the lipid nanoparticles exists in a liquid state at room temperature or in the body, and therefore, they are mixed with the poloxamer base at room temperature to deteriorate the dual-reverse thermosensitive hydrogel formulation. Further, when the melting point of the lipid mixture is higher than 36° C., the lipid nanoparticles are not melted while maintaining a solid form even in the body, and therefore, the drug is not released and efficacy is not obtained.

The dual-reverse thermosensitive formulation according to the present invention may include a stabilizer, and preferably, the stabilizer may be a polysorbate-based stabilizer, for example, one or more selected from the group consisting of Tween 20 (polysorbate 20, polyoxyethylene (20) sorbitan monolaurate), Tween 40 (polysorbate 40, polyoxyethylene (20) sorbitan monopalmitate), Tween 60 (polysorbate 60, polyoxyethylene (20) sorbitan monostearate), and Tween 80 (polysorbate 80, polyoxyethylene (20) sorbitan monooleate). More preferably, the stabilizer may be Tween 80. Preferably, Tween 80 may be included in an amount of 2% by weight to 6% by weight. When Tween 80 is included in an amount of more than 6% by weight, the gelation temperature becomes lower than 30° C., and therefore, the dual-reverse thermosensitive hydrogel composition is in a gel state at room temperature and rectal administration is very difficult. When Tween 80 is included in an amount of less than 2% by weight, the gelation temperature becomes higher than 36° C., the composition maintains a liquid form even in the body, and thus release of the drug is not effectively controlled. Accordingly, it is difficult to control initial burst effect and to avoid direct contact of the drug with the body tissues, and thermosensitive lipid nanoparticles agglomerate with each other to form aggregates to cause a problem in physical stability of the irinotecan-loaded dual-reverse thermosensitive hydrogel composition.

The dual-reverse thermosensitive formulation according to the present invention may be administered via a rectal, transdermal, subcutaneous, intravenous, rectal, or intramuscular route, and preferably, via an intramuscular or rectal route.

The irinotecan-loaded dual-reverse thermosensitive formulation according to the present invention may further include a common pharmaceutically acceptable carrier, excipient, diluent, or subcomponent well known to those skilled in the art.

Effect of the Invention

A formulation including an irinotecan-loaded solid lipid nanoparticle-dispersed thermosensitive hydrogel according to the present invention may release the drug with dual-reverse thermosensitive property, thereby increasing efficacy of irinotecan, and improving initial burst effect of the drug and safety to the body tissues, compared to existing hydrogels.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

FIG. 1 shows a schematic illustration of an irinotecan-loaded dual-reverse thermosensitive formulation according to an exemplary embodiment of the present invention and a dual-reverse phenomenon occurring upon administration of the formulation into the body;

FIG. 2 shows a dissolution test of the irinotecan-loaded dual-reverse thermosensitive formulation according to an exemplary embodiment of the present invention;

FIG. 3 shows blood concentration curves after rectal administration (1) and intramuscular administration (2) of the irinotecan-loaded dual-reverse thermosensitive formulation according to an exemplary embodiment of the present invention into mice;

FIG. 4 shows tumor size (1) and body weight loss (2) curves after repeated rectal administration of the irinotecan-loaded dual-reverse thermosensitive hydrogel composition into tumor-induced mice;

FIG. 5 shows tumor size (1) and body weight loss (2) curves after repeated intramuscular administration of the irinotecan-loaded dual-reverse thermosensitive hydrogel composition into tumor-induced mice; and FIG. 6 shows images of rectal tissue (1) and muscle tissue (2) after rectal administration and intramuscular administration of the irinotecan-loaded dual-reverse thermosensitive hydrogel composition into mice, respectively.

DETAILED DESCRIPTION OF THE EMBODIMENTS

Hereinafter, the present invention will be described in detail with reference to Examples. However, these Examples are for illustrative purposes only, and the scope of the present invention is not intended to be limited by these Examples.

PREPARATION EXAMPLE 1

Measurement of Melting Points of Single Lipids or Mixture Thereof

Melting points of single lipids or mixtures thereof were measured by differential scanning calorimetry (DSC Q20; TA Instruments, New Castle, Del., USA), and the used lipids are shown in Table 1. As a result, when tricaprin and triethanolamine among the tested lipids were mixed at a weight ratio (% by weight) of 10:90 to 100:0, a single peak was observed without separation of the peaks of the melting points, and the melting point was 32-34° C. Therefore, tricaprin and triethanolamine lipids which exit in a solid form at room temperature and in a liquid form at the body temperature were determined as thermosensitive lipids.

TABLE 1

|  | Lipid | Ratio (% by weight) | Melting point (° C.) |
| --- | --- | --- | --- |
| Compritol | Polyethylene glycol (PEG 400) | 5:5 | 72.5 |
|  | Tween 80 | 5:5 | 68 and 79 (two separated peaks) |
|  | Propylene glycol | 5:5 | 69 |
|  |  | 3:7 | 68 |
|  |  | 4:6 | 68 |
|  |  | 6:4 | 69 |
|  |  | 7:3 | 68 |
| Trimyristin | Propylene glycol | 5:5 | 58 |
|  |  | 2:8 | 58.5 |
|  |  | 3:7 | 59 |
| Tricaprylin | Trilaurin | 5:5 | 11.5 and 44.5 (two separated peaks) |
|  | Trimyristin | 5:5 | 11.5 and 56 (two separated peaks) |

TABLE 1-continued

|  | Lipid | Ratio (% by weight) | Melting point (° C.) |
| --- | --- | --- | --- |
| Triethanolamin | Trilaurin | 5:5 | 48 |
|  | Tricaprin | 5:5 | 11 |
|  | Trimyristin | 5:5 | 59 |
|  | Trilaurin | 5:5 | 21 and 49 (two separated peaks) |
|  | Tricaprin | 10:0 | 22.6 |
|  |  | 9:1 | 32.5 |
|  |  | 8:2 | 32.3 |
|  |  | 7:3 | 33.6 |
|  |  | 5:5 | 33.3 |
|  |  | 3:7 | 33.0 |
|  |  | 1:9 | 32.5 |
|  |  | 0:10 | 32.3 |
| Trilaurin | Tricaprin | 5:5 | 11.5 and 44.5 (two separated peaks) |
|  |  | 6:4 | 31.5 and 46 (two separated peaks) |
|  | Propylene glycol | 3:7 | 46.5 |

EXAMPLES 1 to 8

Preparation of Dual-Reverse Thermosensitive Hydrogel Formulations

Tricaprin and triethanolamine were put in a temperature-controlled container, and dissolved at about 45° C., and then completely mixed with irinotecan to prepare lipid nanoparticles. In this regard, the contents of tricaprin and triethanolamine were as in the following Table 2. The lipid nanoparticles were added to part of a poloxamer solution which was prepared by dissolving poloxamer 188, poloxamer 407, and Tween 80 in water, and emulsified in a high pressure emulsifier (Ultra-Turrax, IKA, Guangzhou, China). Then, the remaining poloxamer solution was added thereto, and mixed well to prepare dual-reverse thermosensitive hydrogel formulations of Examples 1 to 8.

TABLE 2

| Item | | Example 1 | 2 | 3 | 4 | 5 | 6 | 7 | 8 |
|---|---|---|---|---|---|---|---|---|---|
| Irinotecan (g) | | 1.0 | 0.1 | 5.0 | 1.0 | 1.0 | 1.0 | 1.0 | 1.0 |
| Lipid (g) | Tricaprin | 7.2 | 9.9 | 1.0 | 7.2 | 7.2 | 7.2 | 7.2 | 7.2 |
| | Triethanolamine | 1.8 | 0 | 4.0 | 1.8 | 1.8 | 1.8 | 1.8 | 1.8 |
| Poloxamer (g) | P188 | 15 | 15 | 15 | 15 | 16 | 15 | 15 | 16 |
| | P407 | 17 | 17 | 17 | 15 | 18 | 17 | 17 | 18 |
| Tween 80 (g) | | 4 | 4 | 4 | 4 | 4 | 2 | 6 | 6 |
| Water (g) | | 54 | 54 | 54 | 56 | 52 | 56 | 52 | 50 |
| Total (g) | | 100 | 100 | 100 | 100 | 100 | 100 | 100 | 100 |

COMPARATIVE EXAMPLES 1 to 5

Preparation of Dual-Reverse Thermosensitive Hydrogel Formulations

The mixtures of tricaprin and triethanolamine were put in a temperature-controlled container, and dissolved at about 45° C., and then completely mixed with irinotecan to prepare lipid nanoparticles. In this regard, the contents of tricaprin and triethanolamine were as in the following Table 3.

The lipid nanoparticles were added to part of a poloxamer solution which was prepared by dissolving poloxamer 188, poloxamer 407, and Tween 80 in water, and emulsified in a high pressure emulsifier (Ultra-Turrax, IKA, Guangzhou, China). Then, the remaining poloxamer solution was added thereto, and mixed well to prepare formulations of Comparative Examples 1 to 5.

TABLE 3

| Item | | Comparative Example 1 | 2 | 3 | 4 | 5 |
|---|---|---|---|---|---|---|
| Irinotecan (g) | | 5.5 | 1.0 | 1.0 | 1.0 | 1.0 |
| Lipid (g) | Tricaprin | 4.8 | 0 | 7.2 | 7.2 | 7.2 |
| | Triethanolamine | 1.2 | 9.0 | 1.8 | 1.8 | 1.8 |

TABLE 3-continued

| Item | | Comparative Example 1 | 2 | 3 | 4 | 5 |
|---|---|---|---|---|---|---|
| Poloxamer (g) | P188 | 15 | 15 | 17 | 15 | 15 |
| | P407 | 14 | 14 | 18 | 17 | 17 |
| Tween 80 (g) | | 4 | 4 | 4 | 1.5 | 6.5 |
| Water (g) | | 55.5 | 57.0 | 51.0 | 56.5 | 51.5 |
| Total (g) | | 100 | 100 | 100 | 100 | 100 |

EXPERIMENTAL EXAMPLE 1

Melting Point of Lipid Nanoparticles

Melting points of lipid nanoparticles of Examples 1 to 8 and Comparative Examples 1 to 5 were measured by differential scanning calorimetry (DSC Q20; TA Instruments, New Castle, Del., USA) (Table 4).

As a result, in Examples 1 to 8 and Comparative Examples 1, 3 to 5, when the lipid nanoparticles were prepared by mixing tricaprin and triethanolamine at a weight ratio of 10:90 to 100:0, irrespective of the amount of irinotecan, thermosensitive lipid nanoparticles having a melting point of 32-34° C., which existed in a solid form at room temperature and in a liquid form at the body temperature, were formed. However, in Comparative Example 2, when triethanolamine was used alone, the lipid nanoparticles having a melting point of 22.6° C. were formed and existed as a liquid both at room temperature and at the body temperature, indicating no formation of thermosensitive lipid nanoparticles.

TABLE 4

| Section | Melting point (° C.) | Encapsulation efficiency ($\times 10^2$ mPa·s) | Gelation temperature (° C.) | syringe-ability (mPa·s) | Gel strength ($\times 10^2$ mPa·s) |
|---|---|---|---|---|---|
| Example 1 | 32.4 | 97.9 ± 7.7 | 32.5 ± 0.4 | 261.1 ± 4.1 | 100.4 ± 1.7 |
| Example 2 | 32.4 | 97.9 ± 7.7 | 32.4 ± 0.4 | 264.3 ± 3.8 | 147.2 ± 3.2 |
| Example 3 | 32.1 | 95.8 ± 3.2 | 33.1 ± 0.4 | 252.5 ± 5.3 | 83.4 ± 6.3 |
| Example 4 | 32.3 | 99.3 ± 9.6 | 34.2 ± 0.4 | 248.4 ± 2.6 | 90.7 ± 4.3 |
| Example 5 | 32.3 | 97.2 ± 4.1 | 30.9 ± 0.4 | 289.3 ± 6.3 | 89.3 ± 4.4 |
| Example 6 | 32.4 | 97.9 ± 7.2 | 34.5 ± 0.4 | 242.1 ± 1.9 | 130.2 ± 10.2 |
| Example 7 | 32.4 | 97.9 ± 7.4 | 31.8 ± 0.4 | 278.4 ± 3.7 | 141.5 ± 11.1 |
| Example 8 | 32.3 | 96.5 ± 4.1 | 30.4 ± 0.4 | 293.1 ± 2.6 | ** |
| Comparative Example 1 | 32.3 | 65.2 ± 9.0 | 36.7 ± 0.4 | 221.7 ± 4.9 | 94.4 ± 3.5 |
| Comparative Example 2 | 22.6 | 98.1 ± 4.3 | 36.5 ± 0.4 | 227.8 ± 3.1 | 152.6 ± 8.2 |
| Comparative Example 3 | 32.2 | 97.6 ± 7.8 | 28.5 ± 0.4 | 331.9 ± 6.5 | 48.3 ± 6.3 |
| Comparative Example 4 | 32.4 | 97.9 ± 7.7 | 36.9 ± 0.4 | 321.2 ± 4.2 | 43.2 ± 5.2 |
| Comparative Example 5 | 32.3 | 96.7 ± 3.8 | 29.1 ± 0.4 | 318.6 ± 2.3 | ** |

EXPERIMENTAL EXAMPLE 2

Encapsulation Efficiency of Lipid Nanoparticles

Each 1 g of the lipid nanoparticles of Examples 1 to 8 and Comparative Examples 1 to 5 was added to 4 ml of a saline solution, stirred, and centrifuged at 20,000 g for 10 min to obtain a supernatant. This supernatant (20 µl) was used to quantify unencapsulated irinotecan by HPLC (Agilent 1260 Infinity; Santa Clara, Calif., USA). In this regard, inertsil ODS-4 C18 (GL Science, 5 µm, 4.6×250 mm) was used as a column, and a mixture of monobasic sodium phosphate (pH 3.1) and acetonitrile (50:50, % by weight) was used as a mobile phase. A column temperature was 40° C., a flow rate was 1.0 ml/min, and UV wavelength was 254 nm. Encapsulation efficiency (%) was calculated as a ratio of the amount of encapsulated irinotecan to the total amount of irinotecan (Table 4). As a result, lipid nanoparticles of Examples 1 to 8 and Comparative Examples 2 to 5 showed encapsulation efficiency of 90% or more, when the amount of irinotecan is smaller than the amount of lipid, that is, 50% or less of the total weight of the lipid nanoparticles. However, as in Comparative Example 1, when the amount of irinotecan is more than 50% of the total weight of the lipid nanoparticles, the lipid nanoparticles showed greatly low encapsulation efficiency of 70%.

EXPERIMENTAL EXAMPLE 3

Gelation Temperature Depending on Content of Thermosensitive Hydrogel

Each 2 g of the dual-reverse thermosensitive hydrogels of Examples 1 to 8 and Comparative Examples 1 to 5 were put in a 10 ml container, together with a magnetic bar, and the container was placed in a thermostat at 4° C. Then, a digital thermometer was placed in the sample so that it was not in contact with the magnetic bar. The temperature was raised at a rate of 1° C./min under stirring at a constant speed. The momentary temperature at which the magnetic bar completely stopped was noted as a gelation temperature (Table 4). As a result, as in Examples 1 to 8, when the amount of poloxamer 188 and poloxamer 407 was 30% by weight to 34% by weight, based on the total weight, and the amount of Tween 80 was 2% by weight to 6% by weight, the gelation temperature was 30-36° C., and thermosensitive hydrogels were formed, which were in a liquid state at room temperature and altered to a gel at the body temperature. However, as in Comparative Examples 3 to 5, when the amount of poloxamer 188 and poloxamer 407 was more than 34% by weight, based on the total weight, or the amount of Tween 80 was more than 6% by weight, the gelation temperature was 30° C. or lower, and the hydrogels were in a gel state both at room temperature and at the body temperature, indicating no formation of thermosensitive hydrogels. Further, as in Comparative Examples 1, 2, and 4, when the amount of poloxamer 188 and poloxamer 407 was less than 30% by weight, based on the total weight, or the amount of Tween 80 was less than 2% by weight, the gelation temperature was 36° C. or higher, and the hydrogels were in a liquid state both at room temperature and at the body temperature, indicating no formation of thermosensitive hydrogels.

EXPERIMENTAL EXAMPLE 4

Measurement of Syringe-ability

To measure viscosity of the dual-reverse thermosensitive hydrogels of Examples 1 to 8 and Comparative Examples 1 to 5, influencing the ease of intramuscular administration, their viscosity was measured at room temperature, and then separation of a needle from a syringe is examined upon injection into the hind limb muscle of a rat. As a result, when the viscosity is 300 mPa or less, it was easy to administer without separating the needle from the syringe, and therefore, the viscosity was determined as an intramuscular injectable viscosity (Table 4). As in Examples 1 to 8 and Comparative Examples 1 to 2, when the amount of poloxamer 188 and poloxamer 407 is 34% by weight or less, based on the total weight, and Tween 80 is 2% by weight or less, the viscosity was 300 mPa·s or less, which allows easy intramuscular injection. However, as indicated in Comparative Examples 3 to 5, when the amount of poloxamer 188 and poloxamer 407 is more than 34% by weight, based on the total weight, and Tween 80 is more than 6% by weight, the viscosity was 300 mPa·s or more, and therefore, an injectable needle and a syringe were separated, and thus administration was not easy.

EXPERIMENTAL EXAMPLE 5

Measurement of Particle Size for Investigating Physical Stability

The dual-reverse thermosensitive hydrohydrogels of Examples 1 to 8 and Comparative Examples 1 to 5 were stored at 25° C. and 30° C. for 4 months, and their particle sizes were examined (Zetasizer Nano ZS (Malvern Instruments, Worcestershire, UK)). As a result, when Tween 80 is less than 2% by weight, the particle size showed a significant difference from about 1,000 nm at 2 months to about 3,000 nm at 4 months, indicating that the particle size gradually increased over time. In contrast, when Tween 80 is 2% by weight or more, the particle size was 150-200 nm even at 4 months and showed no significant difference, indicating physical stability. These results are shown in Table 5.

TABLE 5

| Particle size (nm) (30° C.) | 0 month | 4 months |
| --- | --- | --- |
| Example 1 | 168 ± 7 | 172 ± 9 |
| Example 2 | 180 ± 16 | 192 ± 7 |
| Example 3 | 179 ± 9 | 180 ± 11 |
| Example 4 | 175 ± 9 | 193 ± 9 |
| Example 5 | 182 ± 5 | 187 ± 6 |
| Example 6 | 178 ± 22 | 182 ± 9 |
| Example 7 | 183 ± 7 | 169 ± 5 |
| Example 8 | 162 ± 3 | 171 ± 9 |
| Comparative Example 1 | 159 ± 9 | 181 ± 12 |
| Comparative Example 2 | 188 ± 7 | 192 ± 3 |
| Comparative Example 3 | 177 ± 10 | 188 ± 4 |
| Comparative Example 4 | 174 ± 6 | 2946 ± 369 |
| Comparative Example 5 | 165± | 189 ± 7 |

EXPERIMENTAL EXAMPLE 6

Dissolution Test

Example 1 (corresponding to 20 mg of drug) was put in a semi-permeable membrane tube, together with an irinotecan solution (containing 1% drug) and an irinotecan hydrogel, respectively, and tied to the paddle. 500 ml of water was used to perform a dissolution test in a dissolution apparatus (VISION-6 Classic, Chatsworth, Calif., USA) in accordance with the Dissolution Test Method II (paddle method) in General Test Methods of Korean Pharmacopoeia. The samples were collected at a given time, and the concentration of irinotecan was measured by the above HPLC method to calculate a dissolution rate. The irinotecan hydrogel was composed of 1% irinotecan, 15% poloxamer 407, 17% poloxamer 188, 4% Tween 80 and 54% water. Conditions were a dissolution temperature of 36.5° C., a paddle speed of 100 rpm, and a dissolution time of 8 hours. A dissolution graph is shown in FIG. 2, and Example 1 showed a significant reduction in the dissolution rate, compared to the drug solution and the irinotecan hydrogel. In particular, Example 1 showed a very significant reduction in the initial dissolution concentration. Further, the drug was slowly released for 8 hours. Therefore, unlike common hydrogels, the dual-reverse thermosensitive hydrogel composition doubly regulates release of a drug such as irinotecan first from the thermosensitive solid lipid and then from the thermosensitive hydrogel, thereby solving the problem of initial burst effect.

EXPERIMENTAL EXAMPLE 7

Pharmacokinetics

36 Male Sprague-Dawley rats (weighing 250±20 g) were fasted for 24-36 hours prior to experiments, and then Example 1 was inserted into 4 cm distal to the rectum of 6 rats at a dose of 2 ml/kg (irinotecan of 25 mg/kg). Further, as controls, an irinotecan solution (containing 1% drug) was intravenously administered, and an irinotecan hydrogel was rectally administered into 6 rats in the same manner as the administration of Example 1. Furthermore, Example 1 was administered into the limb muscle of 6 rats at a dose of 2 ml/kg (irinotecan of 25 mg/kg). As controls, the irinotecan solution (containing 1% drug) and the irinotecan hydrogel were intramuscularly administered into 6 rats in the same manner, respectively. The irinotecan hydrogel was composed of 1% irinotecan, 15% poloxamer 407, 17% poloxamer 188, 4% Tween 80 and 54% water. At a given time, 0.2 ml of the blood was collected from the right femoral artery, and centrifuged to obtain a plasma (150 µl). To this plasma, 150 µl of camptothecin (100 µg/ml, acetonitrile) as an internal standard solution was added, and centrifuged at 13,000 g for 10 minutes to precipitate proteins and to obtain a supernatant. This supernatant (10 µl) was subjected to high speed liquid chromatography (HPLC, Agilent 1260 Infinity, Agilent Technologies; Santa Clara, Calif., USA; ODS-4 C18 (GL Science, 5 µm, 4.6×150 mm) at a column temperature of 40° C. using a mixed solution of monobasic sodium phosphate (pH 3.1) and acetonitrile (50:50, % by weight) as a mobile phase at a flow rate of 1 ml/min and UV absorbance of 254 nm to quantify the blood concentration of irinotecan.

A graph of the blood concentration after rectal administration of Example 1 is shown in FIG. 2, and pharmacokinetic parameters are the same as in Table 6. Compared to the hydrogel, Example showed no significant difference, but a low initial blood concentration, and also no significant difference in AUC value, but a slightly increased AUC value. Compared to intravenous administration of the drug solution, it showed about 45% of absolute bioavailability, which was slightly higher than about 40% of absolute bioavailability of the hydrogel. When the dual-reverse thermosensitive hydrogel composition of Example 1 was rectally administered, it doubly regulates release of irinotecan first from the thermosensitive solid lipid and then from the thermosensitive hydrogel, unlike common hydrogels. Therefore, the initial blood concentration was low whereas bioavailability was slightly increased, suggesting that the dual-reverse thermosensitive hydrogel composition has higher bioavailability and less side effects of irinotecan than common hydrogel.

TABLE 6

| Parameter | Drug solution (intravenous administration) | Hydrogel (rectal administration) | Example 1 (rectal administration) |
|---|---|---|---|
| AUC (µg · h/ml) | 104.29 ± 29.58 | 39.38 ± 7.90 | 45.18 ± 12.67 |
| $T_{max}$ (h) | — | 1.41 ± 0.20 | 1.91 ± 0.20* |
| $C_{max}$ (µg/ml) | 83.68 ± 8.86 | 11.15 ± 1.03 | 11.42 ± 0.88 |
| $t^{1/2}$ (h) | 0.92 ± 0.28 | 4.16 ± 2.41 | 4.61 ± 2.06 |
| Kel (h − 1) | 0.79 ± 0.20 | 0.19 ± 0.09 | 0.18 ± 0.09 |

All values expressed as mean ± standard deviation (n = 6).
Significance at *p < 0.05 as compared with drug solution (intravenous administration) and hydrogel (rectal administration).

A graph of the blood concentration after intramuscular administration of Example 1 is shown in FIG. 4, and pharmacokinetic parameters are the same as in Table 7. Compared to the drug solution and the hydrogel, Example 1 showed significantly low blood concentration, AUC, and $C_{max}$ value, in particular, a significantly very low initial blood concentration. Further, the blood concentration of Example 1 was maintained at about 10 µg/ml from 2 hours to 48 hours. In general, high $C_{max}$ value increases efficacy, but also increases intrinsic side effects of a drug. Thus, the low $C_{max}$ value of Example 1 reduces intrinsic side effects of irinotecan. That is, dissolution of the drug in hydrogel is very rapid, and the drug is very rapidly absorbed to show high $C_{max}$ value. Therefore, side effects of the anticancer toxic drug, irinotecan occur. However, unlike common hydrogels, Example 1 doubly regulates release of irinotecan by the solid lipid altered to a liquid form and the hydrogel altered to a gel form in the body. Therefore, the drug is slowly released and absorbed, and it maintains at a low concentration for 48 hours. Accordingly, after administration, the dual-reverse thermosensitive hydrogel composition may maintain efficacy for 48 hours without side effects of irinotecan.

TABLE 7

| Parameter | Drug solution (intramuscular administration) | Hydrogel (intramuscular administration) | Example 1 (intramuscular administration) |
|---|---|---|---|
| AUC (µg · h/ml) | 1034.91 ± 71.70 | 758.98 ± 115.57* | 724.02 ± 117.21* |
| $T_{max}$ (h) | 2.16 ± 0.40 | 1.83 ± 0.75 | 2.83 ± 0.40* |
| $C_{max}$ (µg/ml) | 17.70 ± 1.80 | 11.86 ± 1.96* | 10.05 ± 1.49* |
| $t^{1/2}$ (h) | 11.93 ± 1.95 | 11.88 ± 1.50 | 10.50 ± 1.66 |
| Kel (h − 1) | 0.06 ± 0.01 | 0.06 ± 0.01 | 0.07 ± 0.01 |

All values expressed as mean ± standard deviation (n = 6).
Significance at *p < 0.05 as compared with drug solution (intramuscular administration) and hydrogel (intramuscular administration).

EXPERIMENTAL EXAMPLE 8

Test of Anticancer Activity and Side Effects

Human epidermoid carcinoma KB cell (American Type Culture Collection; Rockville, Md., USA) was plated in a 24-well plate at a density of $8 \times 10^4$ cells/well, and used to examine anticancer efficiency. Next day, when cells reached 60-70% confluence, DMEM cell culture medium was replaced by a fresh culture medium (500 μl/well). $1 \times 10^6$ KB cells in a 0.1 ml buffer solution were subcutaneously injected into the right rear flank of each of 48 5-week old mice, and this day was determined as 0 day. Tumor dimension was measured. When the tumor size reached 100-150 mm³ (day 7), tumor xenograft mice were randomly divided into 8 groups, and experiments were conducted. Mice of 4 groups were rectally administered with Example 1, a control, an irinotecan solution (containing 1% drug), and an irinotecan hydrogel at a dose of 5 mg/kg of irinotecan three times, that is, on 7 day, 10 day, and 13 day, respectively. Further, mice of the other 4 groups were intramuscularly administered with Example 1, a control, an irinotecan solution (containing 1% drug), and an irinotecan hydrogel at a dose of 5 mg/kg of irinotecan three times, that is, on 7 day, 10 day, and 13 day, respectively. In this regard, the control is a buffer solution (pH 7.4) and the irinotecan hydrogel was composed of 1% irinotecan, 15% poloxamer 407, 17% poloxamer 188, 4% Tween 80, and 54% water. At each day, anticancer efficiency and side effects of Example 1 which was rectally or intramuscularly administered to the tumor xenograft mice were compared by measuring tumor size and body weight loss, respectively.

Graphs showing the tumor size and body weight loss after rectal administration of Example 1 are shown in (1) and (2) of FIG. 4. Example 1 showed a significant reduction in the tumor size, compared to the control and the irinotecan solution. Further, Example 1 showed a slight reduction in the tumor size, compared to the hydrogel, but there was no significant difference therebetween ((1) of FIG. 4). Example 1 showed no significant reduction in the body weight, compared to the irinotecan solution, and also no significant reduction in the tumor size, compared to the hydrogel ((2) of FIG. 4). Further, the control showed no body weight loss, because no anticancer drug was administered, but rather, it showed body weight gain, indicating no side effects of body weight loss. It is considered that rectal administration of the dual-reverse thermosensitive hydrogel composition of Example 1 exhibits improved anticancer effects and similar side effects such as body weight loss, compared to common hydrogels.

Graphs showing the tumor size and body weight loss after intramuscular administration of Example 1 are shown in (1) and (2) of FIG. 5. When administered intramuscularly, Example 1 showed a significant reduction in the tumor size, compared to the control and the irinotecan solution (containing 1% drug). Further, Example 1 showed a slight reduction in the tumor size, compared to the hydrogel, but there was no significant difference therebetween ((1) of FIG. 5). Example 1 showed no significant reduction in the body weight, compared to the irinotecan solution and the hydrogel ((2) of FIG. 4). In general, high $C_{max}$ value increases efficacy, but also increases intrinsic side effects of a drug. Thus, the low $C_{max}$ value of Example 1 reduces intrinsic side effects of irinotecan. That is, dissolution of the drug in hydrogel is very rapid, and the drug is very rapidly absorbed to show high $C_{max}$ value. Therefore, body weight loss which is a side effect of the anticancer toxic drug occurs. However, unlike common hydrogels, Example 1 doubly regulates release of irinotecan by the solid lipid altered to a liquid form and the hydrogel altered to a gel form in the body. Therefore, the drug is slowly released and absorbed without initial burst effect, and it maintains at a low concentration for 48 hours. Accordingly, it is considered that intramuscular administration of the dual-reverse thermosensitive hydrogel composition of Example 1 may exhibit anticancer effects similar to common hydrogel, and also greatly improve side effects such as body weight loss.

EXPERIMENTAL EXAMPLE 9

Histopathological Muscular Findings

Pharmacokinetic study after rectal and intramuscular administrations in Experimental Example 8 were completed, and then rectum and muscle tissues were separated from the mice administered with Example 1 and the irinotecan hydrogel, respectively. The tissues were washed with a saline solution, and then fixed in 10% neutral carbonate-buffered formaldehyde. The tissues were embedded in paraffin using an embedding centre, cut into slices, and stained with haematoxylin & eosin. This muscle mucosa was observed under a light microscope (E400, Nikkon, Tokyo, Japan), and glandular changes in epithelial tissues were observed, compared to those in the control rectal or muscular epithelial tissues which were not treated with the drug.

A to C of FIG. 6 are images of the rectal tissues after rectal administration of Example 1 or hydrogel into mice, and as a result, there was no significant difference, compared to normal cells. Further, Table 8 shows histopathological analysis of the rectum after rectal administration. Example 1 showed no significant difference in the mucosal thickness, epithelial thickness, collagen content, and mononuclear cell number, compared to normal cells, suggesting that the dual-reverse thermosensitive hydrogel composition for rectal administration induces no irritation or injury to the rectum. Therefore, it is considered that the dual-reverse thermosensitive hydrogel composition for rectal administration of Example 1 avoids a direct contact of the drug with the rectum to induce no injury to the rectal mucosa, because the toxic irinotecan is encapsulated in the thermosensitive solid lipid.

TABLE 8

| Histopathological findings | Control group | Hydrogel (rectal administration) | Example 1 (rectal administration) |
| --- | --- | --- | --- |
| Muscular epithelial thickness (μm) | 287.76 ± 30.40 | 281.13 ± 25.98 | 289.70 ± 25.15 |
| Muscular epithelial number (fibers mm$^{-2}$) | 37.71 ± 6.60 | 38.19 ± 3.88 | 38.01 ± 3.64 |
| Mononuclear cell number (cells mm$^{-2}$) | 38.06 ± 5.18 | 37.17 ± 5.38 | 37.69 ± 5.22 |
| Collagen content (% mm$^{-2}$) | 139.33 ± 64.82 | 151.67 ± 82.63 | 135.00 ± 64.33 |

All values expressed as mean ± standard deviation (n = 9).

D to E of FIG. 6 are images of the muscular epithelial tissues after intramuscular administration of Example 1 or hydrogel into mice, and as a result, the hydrogel showed a significant difference, compared to normal cells, and induced injury to the muscle tissue, whereas Example 1 showed no significant difference, compared to control normal cells, and induced no injury to the muscle tissue. Further, Table 9 shows histopathological analysis of the muscle after intramuscular administration. The hydrogel showed a significant difference, such as thin muscle fiber, compared to the control normal cells, and it induced muscle damage. In contrast, Example 1 showed no significant difference in the muscle fiber thickness, muscle fiber number, mononuclear cell number, and collagen content, compared to normal cells, suggesting no injury to the muscle. Therefore, hydrogels cause a direct contact of the toxic irinotecan with the muscle tissue to induce injury to the muscle tissue, whereas the dual-reverse thermosensitive hydrogel composition avoids a direct contact of the drug with the muscle tissue to induce no injury to the muscle tissue, because the drug is encapsulated in the solid nanoparticles.

TABLE 9

| Histopathological findings | Control group | Hydrogel (intramuscular administration) | Example 1 (intramuscular administration) |
|---|---|---|---|
| Muscular epithelial thickness (μm) | 50.11 ± 3.09 | 18.81 ± 3.38* | 48.18 ± 5.67 |
| Muscular epithelial number (fibers mm$^{-2}$) | 139.56 ± 9.02 | 146.44 ± 16.88 | 143.44 ± 9.00 |
| Mononuclear cell number (cells mm$^{-2}$) | 12.11 ± 4.14 | 11.89 ± 4.43 | 13.44 ± 6.04 |
| Collagen content (% mm$^{-2}$) | 5.94 ± 1.25 | 5.77 ± 1.13 | 6.13 ± 3.34 |

All values expressed as mean ± standard deviation (n = 9).
Significance at *p < 0.01 as compared with control.

The invention claimed is:

1. An irinotecan-loaded dual-reverse thermosensitive hydrogel composition, comprising:
   (a) a thermosensitive nanoparticle comprising irinotecan as an active ingredient, and a lipid mixture comprising tricaprin and triethanolamine mixed at a weight ratio of 99.9:0.1 to 10:90; and
   (b) a thermosensitive hydrogel having a gelation temperature of 30 to 36° C., comprising poloxamer 188, poloxamer 407 or a mixture thereof, and Tween 80,
   wherein the lipid mixture has a melting point of 30 to 36° C.

2. The irinotecan-loaded dual-reverse thermosensitive hydrogel composition of claim 1, comprising:
   0.1 wt % to 5 wt % of the irinotecan;
   5 wt % to 9.9 wt % of the lipid mixture;
   30 wt % to 34 wt % of the poloxamer 188, the poloxamer 407, or the mixture thereof; and
   2 wt % to 6 wt % of the Tween 80, based on the total weight of the composition.

3. The irinotecan-loaded dual-reverse thermosensitive hydrogel composition of claim 1, comprising poloxamer 188 and poloxamer 407.

4. The irinotecan-loaded dual-reverse thermosensitive hydrogel composition of claim 2, comprising poloxamer 188 and poloxamer 407.

5. The irinotecan-loaded dual-reverse thermosensitive hydrogel composition of claim 1, which is administered intramuscularly or rectally.

6. The irinotecan-loaded dual-reverse thermosensitive hydrogel composition of claim 1, wherein the thermosensitive nanoparticles are dispersed in the thermosensitive hydrogel.

7. The irinotecan-loaded dual-reverse thermosensitive hydrogel composition of claim 2, wherein the thermosensitive nanoparticles are dispersed in the thermosensitive hydrogel.

8. The irinotecan-loaded dual-reverse thermosensitive hydrogel composition of claim 5, wherein the thermosensitive nanoparticles are dispersed in the thermosensitive hydrogel.

* * * * *